United States Patent [19]

Miyao et al.

[11] 4,229,468
[45] Oct. 21, 1980

[54] SKIN TREATMENT COSMETIC COMPOSITION

[75] Inventors: Kohei Miyao, Kokubunji; Yoshitaka Ito, Chigasaki; Tsuneo Wachi, Tokyo, all of Japan

[73] Assignees: Asai Germanium Research Institute, Tokyo; Pola Chemical Industries, Inc, Shizuoka, both of Japan

[21] Appl. No.: 954,825

[22] Filed: Oct. 26, 1978

[30] Foreign Application Priority Data

Nov. 22, 1977 [JP] Japan ................... 52/139427

[51] Int. Cl.² .................................... A61K 31/28
[52] U.S. Cl. .......................................... 424/287
[58] Field of Search ............................... 424/287

[56] References Cited

PUBLICATIONS

Chemical Abstracts 73:15001g (1970).
Chemical Abstracts 80:104171z (1974).

*Primary Examiner*—Jerome D. Goldberg
*Attorney, Agent, or Firm*—Oblon, Fisher, Spivak, McClelland & Maier

[57] ABSTRACT

A skin treatment cosmetic composition comprises an active ingredient of carboxyethyl germanium sesquioxide having the formula $$(Ge.CH_2CH_2.COOH)_2O_3$$

or an alkali metal salt, an ammonium salt, an amine salt or an amide derivative thereof with a vehicle for cosmetic.

9 Claims, No Drawings

SKIN TREATMENT COSMETIC COMPOSITION

BACKGROUND OF THE INVENTION

The present invention relates to a skin treatment cosmetic composition which is useful for skin treatments especially skin smoothing and healing of abnormal pigmentation.

It has been known that certain organogermanium compounds impart an inhibition of proliferation of Ehrlich's ascites carcinoma cells and are also effective for healing various visceral carcinoma, leukemia, liver function diseases, hypertension and climacteric diseases etc.

However, effects of the organogermanium compounds in a skin treatment as a topical external application have not been studied.

The inventors have studied on effects on skin treatments, skin absorbance and stability in a cosmetic composition and have found that certain organogermanium compounds are significantly effective for various dermatoses especially abnormal pigmentation and also effective for skin treatments to impart lustrous skin and to remove wrinkles. Moreover, the inventors have found that the organogermanium compounds are significantly stable in comparison with known active ingredients for abnormal pigmentation such as vitamin C derivatives, glutathione derivatives, and hydrogen peroxide, and they have excellent skin absorption for effective skin treatment.

SUMMARY OF THE INVENTION

It is an object of the present invention to provide a skin treatment cosmetic composition which is effective for skin treatments to give smooth skin and to heal abnormal pigmentation and other dermatoses.

The foregoing and other objects of the present invention have been attained by providing a skin treatment cosmetic composition which comprises an active ingredient of carboxyethyl germanium sesquioxide having the formula $$(Ge.CH_2 CH_2.COOH)_2O_3 \quad (I)$$

or an alkali metal salt, an ammonium salt, an amine salt, or an amide derivative thereof at a ratio of 0.01 to 5 wt. % preferably 0.1 to 1.0 wt. % with a vehicle for cosmetics.

DETAILED DESCRIPTION OF THE PREFERRED EMBODIMENTS

The formula of $(Ge.CH_2 CH_2.COOH)_2O_3$ means

The carboxyethyl germanium sesquioxide can be prepared by reacting trichlorogermanium with acrylonitrile to result β-cyanoethyltrichlorogermanium and hydrolyzing the product in the presence of a mineral acid and reacting it with thionylchloride to result trichlorogermanium propionylchloride and hydrolyzing the product with water.

The process can be shown by the following equations:

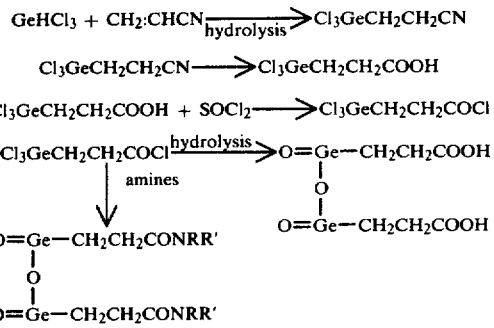

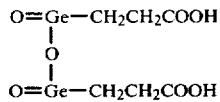

(R and R′=H or an alkyl group ($C_1$ to $C_{12}$))

The carboxyethyl germanium sesquioxide also can be prepared by reacting trichlorogermanium with an alkylacrylate and hydrolyzing the product.

The carboxyethyl germanium sesquioxide can be easily converted to a pharmaceutical salts such as alkali metal salts, ammonium salt, amine salts and also amide derivatives.

Typical salts include salts of sodium, potassium, ammonium, alkylamine, alkanol amine and other amines. Such salts can be formed by a neutralization with the corresponding base.

Typical amide derivatives can be formed by a reaction of an acyl halide form of carboxyethyl germanium compound having the formula $Cl_3GeCH_2CH_2COCl$ with an amine such as alkyl amines and heterocylic amines.

The vehicles for cosmetics can be selected depending upon desired forms of the skin treatment cosmetic compositions.

Typical forms of the skin treatment cosmetic compositions include a cream, an ointment, a lotion, a powder and a cake.

In the form of a cream, water, various fats and oils, esters thereof and emulsifiers and other adjuvants used for preparations of various creams are selectively incorporated.

In the form of an ointment, various fats and oils, esters thereof and emulsifiers and other adjuvants used for preparations of various ointments are selectively incorporated.

In the form of a lotion, water, alcohols and other adjuvants used for preparations of various lotions are selectively incorporated.

In the form of a powder, powdery bases and other adjuvants used for preparations of various powders are selectively incorporated.

These fats and oils, esters, emulsifiers, powdery bases and other adjuvants are well-known by persons skilled in the art, such as Handbook of Cosmetic Science by H. W. Hibbott Pages 229 to 430 published by Pergamon Press (1963).

It is possible to combine the organogermanium compound of carboxyethyl germanium sesquioxide with the other active ingredient for skin-smoothing or melamine-deposition-removement such as vitamin C derivatives and, glutathione derivatives.

When the organogermanium compound is incorporated, as an active ingredient in the skin treatment cosmetic composition, it can be mixed in a crystalline form, an oily form, or a solution form of carboxyethyl germanium sesquioxide, an alkali salt, an amine salt or an amide derivative.

The organogermanium compound is selected depending upon the vehicle for the cosmetic composition.

Excellent skin smoothing effect is attained by applying the cosmetic composition.

The effects of the skin treatment cosmetic compositions of the present invention will be further illustrated.

The skin cream containing sodium carboxyethyl germanium sesquioxide shown in Example 1 is used as Sample I. Sample II as a skin cream is prepared by substituting sodium carboxyethyl germanium sesquioxide with the same amount of vitamin C. distearate in the composition of Sample I. Sample III as a skin cream is prepared by substituting sodium carboxyethyl germanium sesquioxide with the same amount of distilled water in the composition of Sample I.

The following clincal tests are carried out by using the three kinds of Samples I, II and III.

Sixteen females in 32 to 60 ages who have melanosis, are selected as patients and they are grouped into three groups.

Sample I is continuously applied to faces of eight members in the first group and Sample II is continuously applied to faces of four members in the second group and Sample III is continuously applied to faces of four members in the third group for six months respectively. During the test period, members do not use any other skin cream.

The results of the applications of the Samples are evaluated by themselves and doctors.

The results are shown in Table I.

As it is clear from the results of Table I, when Sample I containing sodium carboxyethyl germanium sesquioxide is continuously applied for 6 months, the effects for healing the abnormal pigmentation and the melanostains caused by a parturition or a sunburn are significantly superior to those of the cases applying Samples II or Sample III.

When Sample I is applied, significant cosmetic effects of moisten and lustrous texture smooth skin and removement of wrinkles are found. During the test period, no trouble of dermatoses is found and no side-effect is found.

The acute toxicity of carboxyethyl germanium sesquioxide in oral administration to male rats or female rats is greater than 10 g/kg. In chronic toxicity tests in oral administration for 6 months, at a dose of 30 mg/kg to 3,000 mg/kg per day, no abnormal symptone in various function tests such as normal condition, weight variation, blood, and organ weights is not found and all of rats are survived during six months for the test.

Topical irritation of rabbit by carboxyethyl germanium sesquioxide is studied by the Draize method. Skin irritations such as dermatokelidosis, dermatophyma and dermohemia are not found by applying it in a range of 0.1 to 10 wt. %.

It is confirmed that no topical skin irritation is found at a concentration of less than 1 wt. % in patch tests for human skins.

In tests for skin absorbance of carboxyethyl germanium sesquioxide, Sample I of the skin cream shown in Example I was applied of each back skin of rabbits under preventing a licking by a neck holder and the rabbits are fed in a metabolic cage and urine is sequentially sampled and analyzed by atomic absorptionmetric method to measure a concentration of germanium component in the urine. The excretion of germanium component is continued from 1 hour after the administration to several days and the skin absorption of the compound is confirmed.

These test results show safety and effects of the organogermanium compound as an active ingredient in the skin treatment cosmetic composition.

Heretofore, vitamin C derivatives, glutathione derivatives, hydrogen peroxide and hydroquinone derivatives have been used as active ingredients for healing abnormal pigmentation. However, these active ingredients are easily oxidized or reduced and unstable under an application of heat, light, an acid or a base.

When the active ingredient is incorporated in compositions for external medicines, these active ingredients are gradually decomposed to lose the activity and sometimes changes of color and smell are disadvantageously caused.

On the other hand, the active ingredient of the organogermanium compounds used for skin treatment cosmetic composition of the present invention are significantly stable against heat and light whereby the change of color or smell is not caused and the decomposition and deactivation of the active ingredient in a storage are not caused in the cosmetic compositions. Accordingly, the active ingredient of the present invention can be easily and stably incorporated in various forms of cosmetic compositions advantageously.

An aqueous solution of carboxyethyl germanium sesquioxide (0.6 wt. %) is filled in a colorless glass ampul and is exposed to sunlight for about 3 hours per day and variation of content of carboxyethyl germanium sesquioxide is studied. As the results are shown in Table II, after 12 months, the compound is stable without any decomposition, when the glass ampul is kept in a thermostat constant temperature bath at 50° C. As the results are shown in Table III, after 3 months, the compound is also stable without any decomposition.

When crystal of carboxyethyl germanium sesquioxide is kept at 50° C. for 3 months, no variation of infrared absorption spectrum is found.

TABLE I

| | Patient No. | Age | Abnormal Pigmentation condition | Improvement considered by patients | | |
|---|---|---|---|---|---|---|
| | | | | 2 month later | 4 month later | 6 month later |
| Sample I | 1 | 56 | abnormal pigmentation | ± | ± | + |
| | 2 | 48 | " | + | + | + + |
| | 3 | 43 | " | ± | ± | ± |
| | 4 | 32 | melanostains (sunburn) | ± | ± | + |
| | 5 | 37 | melanostains (sunburn) | + | + | + + |
| | 6 | 46 | melanostains (parturition) | ± | + | + + |
| | 7 | 35 | melanostains | ± | + | + |

TABLE I-continued

| Patient No. | Age | Abnormal Pigmentation condition | Improvement considered by patients 2 month later | 4 month later | 6 month later |
|---|---|---|---|---|---|
| | | (parturition) | | | |
| 8 | 50 | melanostains (parturition) | + | + | ++ |
| Sample II 9 | 45 | abnormal pigmentation | ± | ± | + |
| 10 | 54 | " | − | − | ± |
| 11 | 37 | melanostains (sunburn) | − | ± | + |
| 12 | 39 | melanostains (parturition) | ± | ± | ± |
| Sample III 13 | 60 | abnormal pigmentation | − | ± | ± |
| 14 | 42 | " | − | ± | ± |
| 15 | 39 | melanostains (sunburn) | ± | ± | + |
| 16 | 42 | melanostains (parturition) | − | − | ± |

Degree rating:
− n healing
± substantially no change
+ slightly improved
++ clearly improved

TABLE

| Patient No. | Observation by doctors after 6 months Degree | Observation |
|---|---|---|
| Sample I 1 | improved | color reduced, smoothed skin |
| 2 | excellent | smoothed and lustrous skin |
| 3 | slight | smoothed skin, melanosis remained |
| 4 | improved | smoothed skin |
| 5 | excellent | smoothed skin |
| 6 | excellent | smoothed skin, wrinkles reduced |
| 7 | improved | wrinkles reduced |
| 8 | excellent | smoothed and lustrous skin |
| Sample II 9 | improved | color reduced |
| 10 | non-effective | no healing |
| 11 | improved | skin improved |
| 12 | non-effective | no healing |
| Sample III 13 | non-effective | no healing |
| 14 | non-effective | no healing |
| 15 | improved | skin improved |
| 16 | non-effective | no healing |

TABLE II

| Time | 0 | 3 months | 6 months | 12 months |
|---|---|---|---|---|
| Analyzed by *1 N/10 NaOH (%) | 0.61 | 0.60 | 0.62 | 0.59 |
| Ge content *2 (%) | 0.148 | 0.148 | 0.149 | 0.148 |

*1: Titration with N/10 NaOH
*2: Atomic absorptiometric method

TABLE III

| Time | 0 | 1 month | 3 months |
|---|---|---|---|
| Analyzed by *1 N/10 NaOH (%) | 0.61 | 0.59 | 0.61 |
| Ge content *2 (%) | 0.148 | 0.149 | 0.148 |

The skin treatment cosmetic compositions of the present invention impart excellent effects for removing melamin deposition and for skin-smoothing whereby the compositions are significantly useful as the medicine for external application and the cosmetics and also as a scalp treatment lotion shown in Example 2, an acne treatment lotion shown in Example 3 and a talcum powder shown in Example 4, which are respectively useful for healing depilatory disease and dandruff skin roughness, acne, eczema and body smell. Accordingly, the skin treatment cosmetic compositions of the present invention can be used as medicines, drugs and cosmetics.

The mechanism and function of the organogermanium compound to impart said effects are not clearly understood. Thus, it is considered to improve the skin healing ability by a function for controlling surface membrane potential of biological abnormal cells, and an improvement of biological dehydrogenation based on germanium sesquioxide group, a smoothing of biological oxidation and reduction and an inhibition of peroxidation.

Most important feature of the present invention is to prevent a rough skin and to impart a smooth skin as well as to remove melamin deposition in a skin.

EXAMPLE 1

| Skin cream: | | wt. % |
|---|---|---|
| A | Squalane (dodecahydrosqualone) | 10.0 |
| | Vaseline (petrolatum) | 10.0 |
| | Bees wax | 3.0 |
| | Microcrystalline wax | 9.0 |
| | Spermaceti | 3.0 |
| | Isopropyl myristate | 12.0 |
| | Emulsifier (Nikkol MYS-45) | 4.5 |
| | Emulsifier (Span 60) | 5.0 |
| | Methyl para-hydroxy benzoate | 0.1 |
| B | Propyleneglycol | 10.0 |
| | Sodium carboxyethyl germanium sesquioxide | 0.5 |
| | Distilled water | 32.4 |
| C | Perfume | 0.5 |

The oily components (A) and the aqueous components (B) were respectively heated at 80° C. and they were mixed to emulsify them. During the cooling, the perfume (C) was added under mixing and the skin cream was obtained by cooling the mixture to 30° C.

EXAMPLE 2

| Scalp treatment lotion: | | wt. % |
|---|---|---|
| A | Liquid paraffin | 40.0 |
| | Anhydrous lanolin | 0.5 |
| | Emulsifier (Span 60) | 5.0 |
| B | Salicyclic acid | 0.1 |
| | Propyleneglycol | 2.0 |
| | Distilled water | 50.0 |

-continued

| Scalp treatment lotion: | | wt. % |
|---|---|---|
| C | l-Menthol | 0.1 |
| | Carboxyethyl geramanium sesquioxide | 1.0 |
| | Perfume | 1.2 |

The oily components (A) and the aqueous components (B) were respectively heated to 80° C. and they were mixed to emulsify them. After cooling the mixture to 60° C., the perfume components (C) were added under mixing and the treatment lotion was obtained by cooling the mixture to 30° C.

EXAMPLE 3

| Acne treatment lotion: | wt. % |
|---|---|
| Polyoxyethylene lauryl ether | 1.0 |
| l-menthol | 0.05 |
| Propyleneglycol | 5.00 |
| Sodium carboxyethyl germanium sesquioxide | 0.50 |
| Ethanol | 15.00 |
| Perfume | 0.50 |
| Distilled water balanced to 100 | |

The components were mixed to obtain the lotion.

EXAMPLE 4

| Skin powder: | | wt. % |
|---|---|---|
| A | Talc | 95 |
| | Zinc oxide | 2 |
| | Zinc stearate | 2 |
| | Sodium carboxyethyl germanium sesquioxide | 1 |
| B | Perfume | trace |

The powdery components (A) were thoroughly mixed and the perfume (B) was added to obtain the powder.

What is claimed is:

1. A process for treating the skin to remove abnormal pigmentation and wrinkles and smooth the skin which comprises applying to the skin of patients a cosmetic preparation containing from 0.01 to 5 wt.% thereof of a compound selected from the group consisting of carboxyethyl germanium sesquioxide of the formula $(Ge.CH_2CH_2.COOH)_2O_3$, and its alkali metal, or ammonium salts.

2. The process of claim 1, wherein the compound is carboxyethyl germanium sesquioxide.

3. The process of claim 1, wherein the compound is sodium carboxyethyl germanium sesquioxide.

4. The process of claim 1, wherein the compound carboxyethyl germanium sesquioxide is used in the amount of from 0.1 to 1.0 wt.% of the cosmetic preparation.

5. The process of claim 1, wherein the cosmetic preparation comprises a skin powder containing talc, zinc oxide and zinc stearate.

6. A skin powder for treating abnormal pigmentation comprising 95 wt.% talc, 2 wt.% zinc oxide, 2 wt.% zinc stearate and 1 wt.% sodium carboxyethyl germanium sesquioxide.

7. A skin cream for removing abnormal pigmentation and wrinkles from the skin and smoothing the skin consisting essentially of dodecahydrosqualene and petrolatum as the major skin cream lubricants, beeswax, isopropyl myristate, emulsifier and from 0.01 to 5 wt.% of carboxyethyl germanium sesquioxide, in distilled water.

8. A scalp treatment lotion consisting essentially of liquid paraffin as the major oily component, anhydrous lanolin, emulsifier and from 0.01 to 5 wt.% of carboxyethyl germanium sesquioxide, in distilled water.

9. An acne treatment lotion consisting essentially of polyoxyethylene laurylether, l-menthol, ethanol as the major lotion ingredient and from 0.01 to 5 wt.% of carboxyethyl germanium sesquioxide, in distilled water.

* * * * *